US009659759B2

(12) United States Patent
Panchagnula et al.

(10) Patent No.: US 9,659,759 B2
(45) Date of Patent: May 23, 2017

(54) QUANTITATION OF STRUCTURAL ISOMERS USING MALDI MS/MS

(71) Applicant: COUNCIL OF SCIENTIFIC & INDUSTRIAL RESEARCH, New Delhi (IN)

(72) Inventors: Venkateswarlu Panchagnula, Maharashtra (IN); Nivedita Bhattacharya, Maharashtra (IN); Avinash Dattatraya Ghanate, Maharashtra (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/024,104

(22) PCT Filed: Sep. 25, 2014

(86) PCT No.: PCT/IN2014/000620
§ 371 (c)(1),
(2) Date: Mar. 23, 2016

(87) PCT Pub. No.: WO2015/044958
PCT Pub. Date: Apr. 2, 2015

(65) Prior Publication Data
US 2016/0240362 A1 Aug. 18, 2016

(30) Foreign Application Priority Data
Sep. 25, 2013 (IN) .......................... 1875/DEL/2013

(51) Int. Cl.
*H01J 49/00* (2006.01)
*H01J 49/16* (2006.01)
(Continued)

(52) U.S. Cl.
CPC ........ *H01J 49/164* (2013.01); *G01N 33/6803* (2013.01); *G01N 33/6848* (2013.01);
(Continued)

(58) Field of Classification Search
USPC .................................................. 250/281, 282
See application file for complete search history.

(56) References Cited

U.S. PATENT DOCUMENTS 8,530,831 B1 9/2013 Coon et al.
2002/0019056 A1 2/2002 Shushan et al.
(Continued)

FOREIGN PATENT DOCUMENTS

EP 1876441 A1 1/2008
WO 2007103124 A2 9/2007

OTHER PUBLICATIONS

Guang-Bo Ge, "Stereochemical Difference of C-7 Hydroxyltaxane Isomers by Electrospray Ionization Mass Spectrometry", Rapid Communications in Mass Spectrometry, Feb. 15, 2009, vol. 23, pp. 425-432.
(Continued)

*Primary Examiner* — Nicole Ippolito
*Assistant Examiner* — Hanway Chang
(74) *Attorney, Agent, or Firm* — Baker and Hostetler LLP

(57) ABSTRACT

The present invention relates to a quantitative determination of structural isomers implicated in diseases, the said process is completely independent of chromatographic separation, internal standard, and labeled isotopic references. Further, the present invention provides a diagnostic kit for quantitative determination of structural isomers.

13 Claims, 3 Drawing Sheets

(51) Int. Cl.
*G01N 33/68* (2006.01)
*G06F 19/00* (2011.01)

(52) U.S. Cl.
CPC ............ *G06F 19/70* (2013.01); *H01J 49/004* (2013.01); *H01J 49/0027* (2013.01)

(56) References Cited

U.S. PATENT DOCUMENTS

2008/0274556 A1 11/2008 Cerda et al.
2011/0295521 A1 12/2011 Satulovsky et al.

OTHER PUBLICATIONS

E. Schwedheim, "Quantification of ADMA: Analytical Approaches", Vascular Medicine, Arnold London, vol. I10, No. Suppl. 1, Jan. 1, 2005, pp. S89-S95.
D. H. Chace, "Rapid Diagnosis of Maple Syrup Urine Disease in Blood Spots from Newborns by Tandem Mass Spectrometry", Clinical Chemistry, American Association of Clinical Chemistry, Washington, D.C., vol. 41, No. 1, Jan. 1, 1995, pp. 62-68.

QUANTITATION OF STRUCTURAL ISOMERS USING MALDI MS/MS

CROSS REFERENCE TO RELATED APPLICATIONS

This application is a National Stage of International Application No. PCT/IN2014/000620, filed on Sep. 25, 2014, which claims priority to Indian patent application no. 1875/DEL/2013, filed on Sep. 25, 2013, the disclosures of which are incorporated by reference in their entirety.

FIELD OF THE INVENTION

The present invention relates to a method for quantitatively determining structural isomers implicated in diseases, universally applicable in all concentration ranges of the isomers and that is completely independent of chromatographic separation, internal standard, and labeled isotopic references; of or otherwise using an algorithm. Particularly, the present invention relates to a MALDI MS process for determination of structural isomers quantitatively. More particularly, the present invention also relates to a kit for determination of structural isomers comprising reference standard of isomers, (either in vials or as dried spots on a sample plate) a CD with algorithm for determining the isomers quantitatively, and a detailed protocol to achieve this using the former together.

BACKGROUND AND PRIOR ART OF THE INVENTION

By the year 2030, cardiovascular diseases (CVD) and chronic kidney disorders (CKD) are predicted to be the highest grossing mortality factors worldwide. Screening for biochemical metabolite markers in populations at high risk for these diseases is crucial from a diagnostic point of view.

Various clinical metabolite biomarkers that are implicated in various diseases also have structural isomers, some of which may or may not be implicated in disease manifestations. A few examples for such structural isomers include leucine (Leu)/isoleucine (Ile), associated with diabetes and obesity, asymmetric dimethyl arginine (ADMA)/symmetric dimethyl arginine (SDMA) implicated in cardiovascular diseases or chronic kidney disorders; methylmalonic acid (MMA)/succinic acid (SA) in methylmalonic acidemia; alanine/sarcosine in prostate cancer and bilirubin/lumirubin in neonatal jaundice therapy.

In cases wherein both the isomers are implicated in disease, the ratio of the isomers has been found to be crucial in determining the fate of certain diseases and can independently determine the mortality and morbidity. DMA ratio, known as ADMA catabolism index has been studied as a marker in critically ill patients for organ failure and sepsis. Similarly, co-protoporphyrin isomer ratios are indicative of variegate and hereditary *porphyria*. ADMA, an inhibitor of nitric oxide synthase (NOS) is related to CVD whereas SDMA is a marker for glomerular filtration rate (GFR) and serves as an indicator for CKD. The ratio of ADMA to SDMA is known as ADMA catabolism ratio; this has prognostic value as it determines the extent of accumulation of dimethyl arginine in body.

Leu and Ile are essential branched chain amino acids (BCAA) present only in food. BCAA are important as they are metabolized in the muscles and not in the liver, followed by subsequent conversion to acetyl CoA and succinyl CoA, which are eventually taken up by the tri-carboxylic acid cycle. Therefore, Leu and Ile degradation is altered in people suffering from liver disease, diabetes and obesity.

The conversion of methylmalonyl CoA to succinyl CoA, which requires the presence of vitamin B-12 (Vit-B12) is an important biochemical reaction in the degradation pathway of Ile. Deficiency of Vit-B12 leads to accumulation of MMA in blood leading to methylmalonic acidemia. MMA is a specific indicator for Vit-B12 deficiency and is also observed in patients suffering from cardiovascular ailments and neonatal disorders. SA is interference for MMA in chromatographic separations and a structural isomer of MMA.

Significantly, distinguishing and determination of structural isomer pairs of Leu/Ile, MMA/SA and ADMA/SDMA gives insights into intricate disease linkages between CVD, CKD, and diabetes. Other structural isomers that are implicated in diseases are bilirubin/lumirubin; retinoic acid isomers (vitamin-A deficiency); glucose/fructose and alanine/sarcosine. Infantile jaundice is treated with phototherapy where newborns are exposed to different light wavelengths and bilirubin levels are reduced in due course of time. With phototherapy, bilirubin is converted to its different isomers, a few are configurational isomers, whereas, the other one is a structural one, lumirubin. The structural isomer of sarcosine is L-alanine and has been implicated as a biomarker in progression of prostate cancer.

These conversions are considered as indicators for effective treatment of infantile jaundice. The monosaccharide isomers glucose and fructose is another pair of structural isomers. Alterations in enzymatic conversion of fructose to glucose lead to accumulation and subsequent conversion of fructose to fat. In recent years, adulteration of food with high fructose corn syrup has caused concerns as fructose has been linked with obesity and diabetes.

From the environmental point of view, the pesticide 2,2-bis(4-chlorophenyl)-1,1,1-trichloroethane (DDT) and its structural isomer (2-(2-chlorophenyl)-2-(4-chlorophenyl)-1,1,1-trichloroethane) are also routinely screened from environmental matrices.

In view of the above, structural isomer separation and detection is of vital importance with applications in diverse areas such as disease environmental, pesticides, diagnosis, food and nutrition, drug synthesis and development.

However, it is difficult and challenging to detect these isomers from complex biological mixtures using existing analytical techniques and methodologies. Conventional methods employed include chromatography based separation with or without derivitization and studying them using mass spectrometry. Routine chromatographic techniques namely, liquid and gas chromatography coupled with tandem mass spectrometry (MS/MS) are the usual ways of detecting Ile/Leu, MMA/SA, ADMA/SDMA, glucose/fructose. Alternative techniques such as ELISA (ADMA/SDMA), UV (bilirubin/lumirubin) are also used for differentiation of isomers. Alanine/sarcosine is conventionally separated by GC-MS though;

recently differential mobility tandem mass spectrometry was used for their differentiation. Interestingly, the absolute concentration of the isomer pair (together, not the individual isomers) has often been reported in literature. Often biotransformations and/or interconversions from one isomer form to another are missed out and if a method does not take into account the individual isomer contributions or only screens for only one of the isomers. For example, DDT and its environmental degradation are monitored but, not all studies report the altering ratios of the individual DDT isomers subsequently occurring with biodegradation. This aspect of contributions of individual isomers that form a structural pair in clinical context and their biochemical fate are of significant importance. In analytical and pathological laboratories, knowledge of the relative variation of analyte levels, for example in a diseased state as compared to the baseline healthy or normal subjects is important. By extension, in the case of structural isomers, this relative variation of the individual isomers in a pair is important.

The overall approaches that involve absolute or relative concentrations currently in use have the following disadvantages: (a) limiting due to internal standards and isotopes that many times are either not available or may not be optimized when used with mass spectrometry based quantitation (b) cumbersome with multiple steps, and requiring different set of calibrators for different concentration ranges and (c) may propagate systemic errors affecting the quantitation.

Additionally, these methods also suffer from lack of throughput needed for the analysis of large numbers of samples; require either an internal standard or isotope labelled standard for quantitation.

Isomer detection and quantitation using mass spectrometry has been used previously especially along with chromatographic techniques that aid in isomer separation prior to mass analysis. A few reports and patents are also available, though most of the methods have been developed using triple/quadruple instruments equipped with single/multiple reaction monitoring platforms.

Matrix-assisted laser desorption/ionization tandem mass spectrometry (MALDI-MS/MS) is a chromatographic separation free method and at the same time enables high throughput processing of samples. Label free mass spectrometry methods reduce the cost of analysis and bypasses synthesis for a particular isotope label incorporated chemical entity. It is challenging to synthesize chemical structures containing labels and practically impossible for untargeted, unknown and unpredicted structures that usually span the entire mass spectrum range.

Any quantitative method requires normalization of data; in mass spectrometry exogenous internal standards serve that purpose. Tandem mass spectrometry relies on reference standards generally labelled with stable isotopes for that purpose. However, it is possible to achieve normalization without using an exogenous internal standard.

In a Perkin Elmer patent having WIPO Publication No. WO/2007/103124 disclose a method of differentiation of ADMA and SDMA in a mixture using electrospray ionization tandem mass spectrometry (ESI-MS/MS), however, the method uses an isotopic label as an internal standard for quantitation.

Furthermore, handling and processing all the data generated by analytical techniques requires software that gives the required output based on peak area/intensity. This removes any human errors and increases the throughput of the analysis significantly. In some cases the data processing could involve multiple steps that are difficult and time consuming if performed manually without using an algorithm. Any clinical diagnostic application needs throughput. MALDI MS/MS offers high throughput along with sensitive analysis. However, any high throughput technique generates large volumes of data that can only be managed using algorithms. Thus, high throughput platforms such as MALDI/MS estimating structural isomers from mixtures used for high throughput analysis implies generation of large amount of data alongside and thus, software that can process, distinguish, model, quantify and estimate diagnostic values holds clinical significance.

Bearing in mind the above requirements for quick analysis, the instant inventors have used an in-house developed algorithm, which can quantify isomers identified based on their exact masses' using the respective peak heights or areas. The instant method does not require chromatographic separation, significantly reduces the analysis time and greatly simplifies the analysis. Thus, analytical methods, processes and algorithms developed to work with the method to estimate isomers make them more user friendly and enable large scale implementation for societal use and wider access of diagnostic tools.

In the light of the foregoing there is a need in the art to develop a method for identification and quantification of the structural isomers in a mixture that is devoid of the requirements of isotopic labeling, internal standards, and chromatographic separations.

The focus of the instant invention pertains to isotopic label and internal standard free, chromatography free quantitative analysis of tandem mass spectra obtained for structural isomers and interpreted/processed by an algorithm developed in-house. And applicability of methods using these for diverse sets of end applications whose use includes mass spectrometry, cover multiple chemical entities and their varying concentrations (spanning a range of milli grams to femto grams in a unit volume) in a given sample.

OBJECTS OF THE INVENTION

Main object of the present invention is to develop quantitative models of structural isomers from an equimolar mixture of the same.

Another object of the present invention is to provide quantitative parameters which are chosen based upon peak intensity or peak area from tandem MS spectra which is normalized using common peak arising from the isomers.

Yet another object of the present invention is to provide quantitation of these isomers from any unknown samples having stoichiometric ratios of the same such that the total number of moles is equal.

Yet another object of the present invention is to provide the end-user with a kit (shown in FIG. 2 and FIG. 6 in a plate format with dried spots) that contains a series of standards containing equimolar mixture, biological fluid including simulated or synthetic bio-fluid spiked with equimolar mixture for ready use, necessary solutions such as appropriate buffers or appropriate solvent mixtures, a CD containing algorithm and a detailed protocol for analysis.

SUMMARY OF THE INVENTION

Accordingly, present invention provides a method for quantitatively determining structural isomers independent of the concentration of isomers, chromatographic separation, internal standard and labelled isotopic references comprising:

a) subjecting an equimolar mixture containing the reference isomers to ionization and selecting precursor ions having a mass to charge ratio in an m/z range between 1 to 400000 (z=1) followed by fragmentation to generate product ions that are both common and unique in nature to the reference isomers;

b) selecting product ions that are common to the isomer pairs to normalize the unique product ions followed by measuring the peak area/peak intensity ratios of the unique and common product ions to generate equimolar concentration response curves for each individual isomer pair as a function of equimolar ratios; and c) subjecting a sample containing unknown quantities of the isomers/isomer pairs in context, measuring the unique to common product ion ratio(s), and determining the corresponding equimolar ratio(s) of the isomer pairs present based on the equimolar concentration response curve(s) generated in step (b).

In an embodiment of the present invention, the equimolar reference mixture is selected from a single pair of isomers and/or multiple pairs of different isomers mixed together to make a single or several sets of reference equimolar mixture(s).

In another embodiment of the present invention, the analyte is subjected to MALDI MS/MS or LDI MS/MS analysis or the product ions are generated in the MS mode through a fragmentation process such as post source decay.

In yet another embodiment of the present invention, the common product ions are from the said analyte or a different analyte fragmenting together with analyte.

In yet another embodiment of the present invention, the peak area/peak intensity ratios of unique and common product ions to generate concentration response curves are based on the ASCII files.

In yet another embodiment of the present invention, the isomers are selected from the group consisting of asymmetric dimethyl arginine (ADMA) and symmetric dimethyl arginine (SDMA); leucine and isoleucine; methyl malonic acid (MMA) and succinic acid (SA); bilirubin and lumirubin and the like.

In yet another embodiment of the present invention, the sample is a biological sample selected from urine, blood sample, blood plasma or RBC from patient samples or any other such sources of the isomers.

In yet another embodiment of the present invention, the method for quantitatively determining asymmetric dimethyl arginine (ADMA) and symmetric dimethyl arginine (SDMA) comprises:
  a) subjecting an equimolar mixture containing the reference isomers i.e. ADMA and SDMA to ionization and selecting ions having a mass to charge ratio in an m/z range followed by fragmentation to generate product ions that are unique and common to the ADMA and SDMA;
  b) selecting a common product ion at m/z 116 to normalize the product ion unique to ADMA at m/z 46 and SDMA at m/z 172 respectively, followed by measuring the peak area/peak intensity ratios of the unique and common product ions to generate concentration response curves; and
  c) subjecting a sample containing unknown concentrations of ADMA and SDMA isomers followed by measuring the unique to common product ion ratio(s), and determining the corresponding equimolar ratio(s) of the isomer pairs present based on the equimolar concentration response curve(s) generated in step (b).

In yet another embodiment of the present invention, the equimolar reference mixture is selected from a single pair of ADMA and SDMA and/or multiple pairs of ADMA and SDMA mixed together to make a single or several sets of reference equimolar mixture(s).

In yet another embodiment of the present invention, the method for quantitatively determining isomers leucine and isoleucine comprises:
a) subjecting an equimolar mixture containing the reference isomers i.e. leucine and isoleucine to ionization and selecting ions having a mass to charge ratio in an m/z range followed by fragmentation to generate product ions that are unique and common to the leucine and isoleucine;
  b) selecting a common product ion at m/z 44 to normalize the product ion unique to isoleucine at m/z 18 followed by measuring the peak area/peak intensity ratios of the unique and common product ions to generate concentration response curves; and
  c) subjecting a sample containing unknown concentrations of leucine and isoleucine followed by measuring the unique to common product ion ratio(s), and determining the corresponding equimolar ratio(s) of the isomer pairs present based on the equimolar concentration response curve(s) generated in step (b)—using algorithm 'EquiMQ'.

In yet another embodiment of the present invention, the equimolar reference mixture is selected from a single pair of leucine and isoleucine and/or multiple pairs of leucine and isoleucine mixed together to make a single or several sets of reference equimolar mixture(s).

In yet another embodiment of the present invention, the method for quantitatively determining isomers methyl malonic acid and succinic acid comprises:
  a) subjecting an equimolar mixture containing the reference isomers i.e. methyl malonic acid and succinic acid to ionization and selecting product ions having a mass to charge ratio in an m/z range followed by fragmentation to generate product ions that are unique and common to methyl malonic acid and succinic acid;
  b) selecting a common product ion at m/z 73 to normalize the product ion unique to succinic acid at m/z 98 followed by measuring the peak area/peak intensity ratios of the unique and common product ions to generate concentration response curves;
  c) subjecting a sample containing unknown concentrations of methyl malonic acid and succinic acid followed by measuring the unique to common product ion ratio(s), and determining the corresponding equimolar ratio(s) of the isomer pairs present based on the equimolar concentration response curve(s) generated in step (b).
  d)

In yet another embodiment of the present invention, the equimolar reference mixture is selected from a single pair of methyl malonic acid and succinic acid and/or multiple pairs of methyl malonic acid and succinic acid mixed together to make a single or several sets of reference equimolar mixture(s). In yet another embodiment of the present invention, a method of diagnosing a disease caused by altered concentrations of isomer ratio by measuring the ratio of the isomers in a biological sample, which process comprises:
  a) isolating and providing a biological sample from a subject;
  b) subjecting an equimolar mixture containing the reference isomers to ionization and selecting product ions having a mass to charge ratio in an m/z range followed by fragmentation to generate product ions that are both common and unique in nature to the reference isomers;
  c) selecting product ions that are common to the isomer pairs to normalize the unique product ions followed by measuring the peak area/peak intensity ratios of the unique and common product ions to generate equimolar concentration response curves for each individual isomer pair as a function of equimolar ratios; and
  d) subjecting a sample containing unknown quantities of the isomers/isomer pairs in context, measuring the unique to common product ion ratio(s), and determining the corresponding equimolar ratio(s) of the isomer pairs present based on the equimolar concentration response curve(s) generated in step (b).

wherein altered ratio of isomers in the biological sample compared to the reference is indicative that the subject has, or is at a risk of developing a disease characterized, by altered ratio of the isomer.

In yet another embodiment of the present invention, the disease is a cardiovascular disease or a chronic kidney disease, liver disorders, maple syrup urine disease, diabetes, obesity, methylmalonic acidemia, vitamin B12 deficiency and pernicious anemia.

In yet another embodiment of the present invention, a method of diagnosing a disease caused by altered concentrations of ADMA and SDMA ratio by measuring the ratio of the isomers in a biological sample, which process comprises:
a. isolating and providing a biological sample from a subject;
b. subjecting an equimolar mixture containing the reference isomers ADMA and SDMA to ionization and selecting product ions having a mass to charge ratio in an m/z range followed by fragmentation to generate product ions that are unique and common to ADMA and SDMA;
c. selecting a common product ion at m/z 116 to normalize the product ions unique to ADMA at m/z 46 and SDMA at m/z 172 followed by measuring the peak area/peak intensity ratios of the unique and common product ions to generate concentration response curves; and
d. subjecting a sample containing unknown concentrations of ADMA and SDMA isomers followed by measuring the unique to common product ion ratio(s), and determining the corresponding equimolar ratio(s) of the isomer pairs present based on the equimolar concentration response curve(s) generated in step (b);

wherein altered ratio of ADMA:SDMA in the biological sample compared to the reference is indicative that the subject has, or is at a risk of developing a disease characterized by altered ratio of ADMA:SDMA.

In yet another embodiment of the present invention, the disease is a cardiovascular disease or a chronic kidney disease.

In yet another embodiment of the present invention, a method of diagnosing a disease caused by altered concentrations of leucine and isoleucine ratio by measuring the ratio of the isomers in a biological sample, which process comprises:
a) isolating and providing a biological sample from a subject;
b) subjecting an equimolar mixture containing the reference isomers leucine and isoleucine to ionization and selecting product ions having a mass to charge ratio in an m/z range followed by fragmentation to generate product ions that are unique and common to the leucine and isoleucine;
c) selecting a common product ion at m/z 44 to normalize the product ion unique to isoleucine at m/z 18 followed by measuring the peak area/peak intensity ratios of the unique and common product ions to generate concentration response curves; and
d) subjecting a sample containing unknown concentrations of leucine and isoleucine followed by measuring the unique to common product ion ratio(s), and determining the corresponding equimolar ratio(s) of the isomer pairs present based on the equimolar concentration response curve(s) generated in step (b).

wherein altered ratio of leucine:isoleucine in the biological sample compared to the reference is indicative that the subject has, or is at a risk of developing a disease characterized by altered ratio of leucine:isoleucine.

In yet another embodiment of the present invention, the disease is selected from liver disorders, maple syrup urine disease, diabetes and obesity.

In yet another embodiment of the present invention, a method of diagnosing a disease caused by altered concentrations of methyl malonic acid and succinic acid isomer ratio by measuring the ratio of the isomers in a biological sample, which process comprises:
a) isolating and providing a biological sample from a subject;
b) subjecting an equimolar mixture containing the reference isomers methyl malonic acid and succinic acid to ionization and selecting product ions having a mass to charge ratio in an m/z range followed by fragmentation to generate product ions that are unique and common to methyl malonic acid and succinic acid;
c) selecting a common product ion at m/z 73 to normalize the product ions unique to succinic acid at m/z 98 followed by measuring the peak area/peak intensity ratios of the unique and common product ions to generate concentration response curves; and
d) subjecting a sample containing unknown concentrations of methyl malonic acid and succinic acid followed by measuring the unique to common product ion ratio(s), and determining the corresponding equimolar ratio(s) of the isomer pairs present based on the equimolar concentration response curve(s) generated in step (b).

wherein altered ratio of methyl malonic acid and succinic acid in the biological sample compared to the reference is indicative that the subject has, or is at a risk of developing a disease characterized by altered ratio of methyl malonic acid and succinic acid.

In yet another embodiment of the present invention, the disease is selected from methylmalonic acidemia, vitamin B12 deficiency and pernicious anemia.

In yet another embodiment, present invention provides a diagnostic kit for determination of structural isomers comprising:
a) equimolar mixture of reference standards of isomer(s) pairs in vials and/or as dried precoated spots on a sample analysis plate,
b) a CD with algorithm for determining the isomers quantitatively, and
c) a detailed protocol to achieve this using the former together.

In yet another embodiment, present invention provides a diagnostic kit comprising:
a) a series of mixture of isomers in varying ratios;
b) three quality control samples in plasma or any such fluid from biological source or synthetically simulated, and standards;
c) solutions/buffers (labeled as Buf1-Buf3); and/or
d) a disposable MALDI target plate containing dried spots of Clinical Isomer Pairs (CIP-ADMA/SDMA, Leu/Ile and MMA/SA) mixture along with space for samples to be analyzed; and
e) software on a CD and instructions to use the kit contained in a Product Information Sheet.

DETAILED DESCRIPTION OF THE INVENTION

Figure 1:
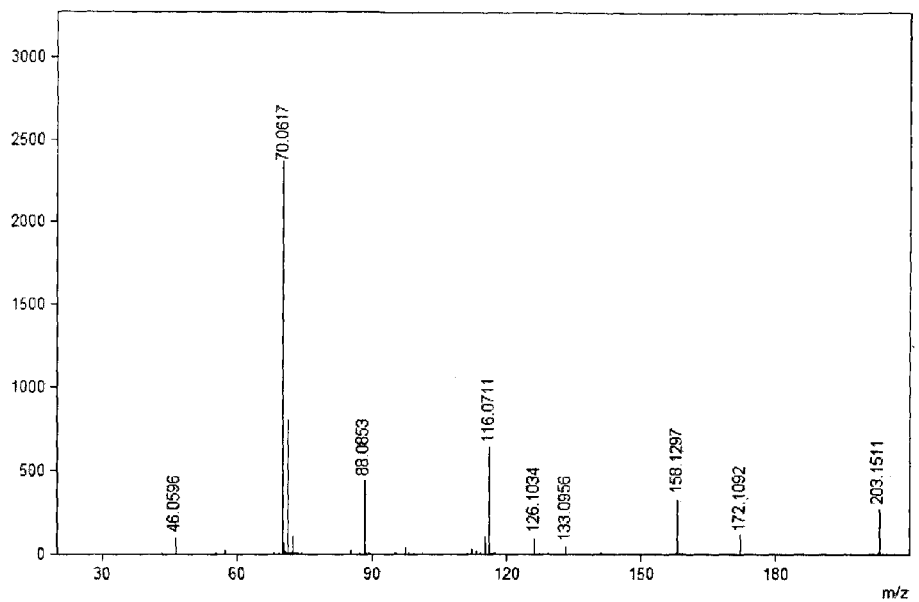
FIG. 1 depicts MALDI MS/MS of a structural isomer pair, ADMA and SDMA in a mixture.
Figure 2:
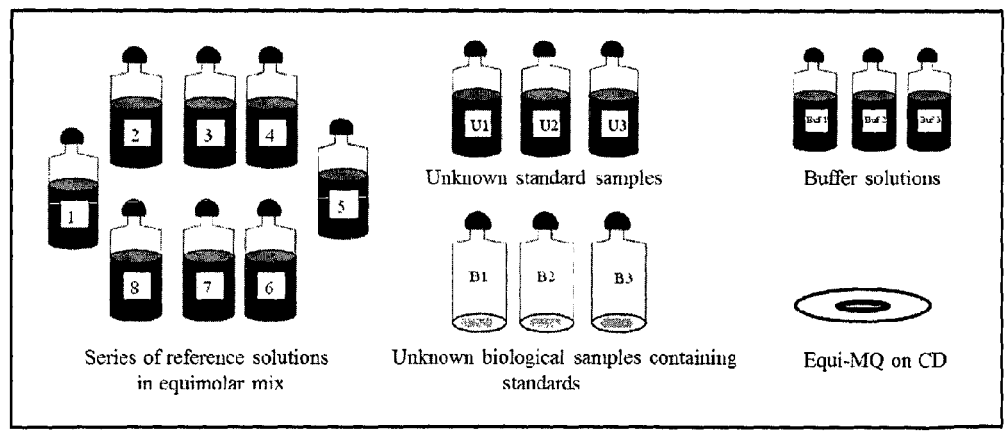
FIG. 2 depicts a diagrammatic representation of a kit containing bottles with numbers 1, 2, 3 . . . 8 as reference solutions, unknown standard samples labeled as U1, U2, U3, unknown biological samples as B1, B2, B3, buffer solutions: Buf 1, Buf 2, Buf 3 and CD with algorithm for analysis: Equi-MQ.
Figure 3:
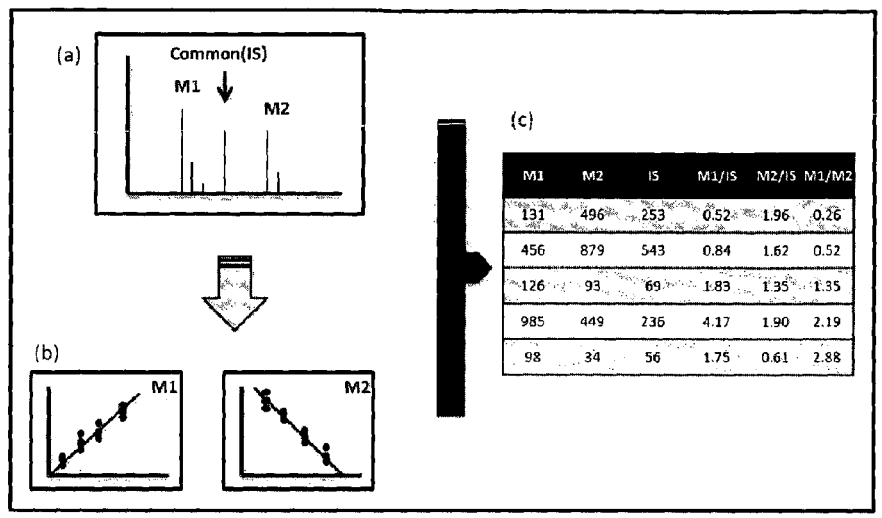
FIG. 3 depicts a workflow representation of algorithm used in Equi-MQ with following steps (a) Identification of peaks for unique as well as common fragments of structural isomers from 'm' spectrum, and determination of quantitative parameters for these peaks using peak area or peak intensities (b) Building quantitative models using common peak as normalizing factor (c) Quantitation of individual structural isomers from QC or unknown samples.

A few structural isomers are known to influence the outcome of certain diseases. Several others are found in diverse applications, many of which are non clinical. Distinguishing and quantifying these isomers using any analytical platform, especially a sophisticated technique such as mass spectrometry, is difficult. Generally, mass spectrometry methods coupled with chromatography are used for differentiating these isomers based on different product ions arising due to different structures. However, these methods are quite tedious because of the complexities introduced by labor-intensive sample preparation with chromatographic separations, reaction monitoring schemes that despite being selective suffer from poor mass accuracies, heavy duty cycle for ion selections. Apart from this, for normalization of mass spectra obtained, an exogeneous, stable isotope is required as an internal standard. The stable isotope in some cases is difficult to synthesize and are expensive.

In this invention, structural isomers are detected and quantitated with MALDI-TOF MS from an equimolar mixture of the isomers independent of any chromatographic separation, reaction monitoring scheme, isotope label and internal standard, however, with an algorithm 'equi-MQ' developed in-house.

EquiMQ is an inhouse developed software for high-throughput quantitation of structural isomers using MALDI MS/MS. It is a generic tool and operating system independent with easy to use features. It requires data in ASII file format containing pair values for m/z and intensity values. EquiMQ incorporates modules like data visualization, quantitation of analytes, based on mass accuracy. This tool offers two quantitative parameters to choose for user flexibility which are, peak intensity and area under the curve that are reported in previous studies. For peak intensity, peak with maximum intensity is chosen from spectral region encompassing data points from allowed PPM error in vicinity of calculated exact mass value for the analyte. While, for peak area under the curve a polynomial function of order 3 is fitted to these data points and then the area under this polynomial curve is used. One of these methods can be used to identify the quantitative parameters for the distinguishing as well as common ions for the isomers. Currently, EquiMQ supports simultaneous modeling for the following adducts formations in the analytes: protonated, sodiated, potassiated, lithiated, and doubly-lithiated. After normalization of the distinguishing ion peak using common ion peak quantitative parameters, a linear regression model is fitted to the data. These calibration models were used to identify the specific isomer concentration from an unknown sample. The present invention provides for the quantification of isomers selected from the group consisting of asymmetric dimethyl arginine (ADMA) and symmetric dimethyl arginine (SDMA); leucine and isoleucine; methyl malonic acid (MMA) and succinic acid (SA); bilirubin and lumirubin and the like. In an aspect, the present invention provides a method for quantitatively determining structural isomers independent of the concentration of isomers, chromatographic separation, and internal standard labelled or otherwise comprising:

a) subjecting an equimolar mixture containing the reference isomers to ionization and selecting precursor ions having a mass to charge ratio in an m/z range followed by fragmentation to generate product ions that are both common and unique in nature to the isomers;

b) selecting product ions that are common to the isomer pairs to normalize the unique product ions followed by measuring the peak area/peak intensity ratios of the unique and common product ions to generate equimolar concentration response curves for each individual isomer pair as a function of equimolar ratios; and c) subjecting a sample containing unknown quantities of the isomers/isomer pairs in context, measuring the unique to common product ion ratio(s), and determining the corresponding equimolar ratio(s) of the isomer pairs present based on the equimolar concentration response curve(s) generated in step (b).

The case is presented here with the example of structural isomers of ADMA/SDMA, Leu/Ile and MMA/SA that influences the outcome of cardiovascular disease (CVD), chronic kidney disorder (CKD) and diabetes. These isomers are differentiated by peaks at m/z 46 and 172 (shown in Figure/Drawing 1) for ADMA and SDMA, respectively. They share all other product ions as common ions. Thus, in a series of equimolar mixture solutions, wherein total number of moles is maintained constant, the differentiating product ions are contributed by the isomers that will vary according to the concentration of the respective isomer present in the mixture, whereas, the common product ions are constant throughout the series. Hence, common product ions can be used as internal standard for normalization of mass spectral data and generate quantitative models using 'equi-MQ' based on peak intensity or area. The obtained quantitative models are further validated using the quality control or unknown (QC) samples from standards and biological fluids.

The invention can be summarized as a high throughput, algorithm assisted method for detection and quantification of structural isomers in an equimolar mixture. This method is devoid of chromatographic separation, and needs neither internal standards nor isotope labelling for structural isomer analysis. High throughput method according to the invention offers quick analysis desired in a clinical laboratory. Further, an algorithm assisted method removes any bias and complements the throughput with analytical rigor. The inventive methods that are devoid of separation techniques, internal standard and isotope labels, are time-saving, require less sample preparation and are robust.

In another aspect, the present invention provides a diagnostic kit for determination of structural isomers comprising:
a) equimolar mixture of reference standards of isomer(s) pairs in vials and/or as dried precoated spots on a sample analysis plate,
b) a CD with algorithm for determining the isomers quantitatively, and
c) a detailed protocol to achieve this using the former together.

The kit offers end-user an assay for measuring structural isomers from their samples. Thus, the quantitation method described herein using ratios of unique product ions of isomeric analytes with respect to the common product ions is a suitable alternative for detecting and quantifying these isomers from a complex mixture. This method is applicable over a wide concentration range and uses a single set of equimolar quantities of isomer pair(s) in a mixture.

The present invention provides an equimolar reference mixture containing either a single pair of isomers or multiple pairs of different isomers mixed together to make a single or several sets of reference equimolar mixture(s).

The method for quantifying structural isomers comprises:
a) Preparing a series of isomer mixture from synthetic standards in stoichiometric ratio such that all the samples in series are equimolar;
b) Loading samples prepared in step (a) on a MALDI or LDI target plate and subjecting the samples to MALDI MS/MS or LDI MS/MS analysis;
c) Subsequent software enabled measurement of peak area/peak intensity ratios of unique and common product ions to generate concentration response curves based on the ASCII files (the common product ion can be from the analyte or a different analyte fragmenting together with analyte);
d) To validate the obtained calibration curve, unknown amounts of the isomers were spiked in biological specimen such as blood, urine, saliva, tissue as quality control (QC) samples. The algorithm determines the QC samples' concentration based on the obtained calibration parameters;
e) Implement the QC validated method and algorithm to detect the isomers from unknown samples such as urine, blood plasma or RBC from patient samples or any other such sources of the isomers and generate a report for use by Physicians or relevant practitioners, and
f) Determination of the ratios of the isomers from the calibration curves and unknowns in a high-throughput method that can be applied in a clinical laboratory and others based on the relevant application in context.

In an embodiment the present invention provides a quantitative MALDI MS/MS data analysis with the in-house developed software to distinguish isomers in a mixture based on peak area or peak height of unique product ions belonging to each isomer, normalized with a common product ion attributed to both and generate model-fitted curves as responses based on the different concentrations (workflow is shown in Figure/Drawing 3).

The in-house software 'Equi-MQ' developed is unique in distinguishing isomers in stoichiometric ratios as it relies, on exact masses and can generate quantitative models approximating the tandem mass responses for the varied ratios. 'Equi-MQ' can also generate models for isomer quantitation depending on linear or non-linear behavior.

'Equi-MQ' can determine ADMA catabolism index based on the varied ratios of ADMA and SDMA. Hence, it can be further used as a predictive tool in disease diagnosis.

Quantitation using other tandem mass spectrometry based methods for these analytes relies on SRM and MRM where the calibration parameter (peak area/peak intensity) is normalized with a heavier isotope. The present method bypasses the use of an external labeled standard with a common product ion that arises from both ADMA and SDMA as in an equimolar mixture; considering the contribution of a common product ion would be same from both isomers.

In another embodiment the present invention provides that in a diseased state if the isomers concentration is known to be altered and their ratio is an index of prognosis, software can estimate the ratio and thus, help in diagnosis.

Further, the present invention provides a method of simultaneous MALDI MS/MS monitoring of isomer unique product ions in a mixture irrespective of setting up selected or multiple ion monitoring schemes (SRM and MRM, respectively).

In yet another embodiment, the present invention provides for the quantification of isomers selected from the group consisting of asymmetric dimethyl arginine (ADMA) and symmetric dimethyl arginine (SDMA); leucine and isoleucine; methyl malonic acid (MMA) and succinic acid (SA); bilirubin and lumirubin and the like.

Accordingly, in a preferred embodiment, the present invention provides a process for quantitatively determining asymmetric dimethyl arginine (ADMA) and symmetric dimethyl arginine (SDMA) comprising:
a) subjecting an equimolar mixture containing the reference isomers ADMA and SDMA to ionization and selecting precursor ions having a mass to charge ratio in an m/z range followed by fragmentation to generate product ions that are common and unique to ADMA and SDMA;
b) selecting a common product ion at m/z 116 to normalize the product ions unique to ADMA at m/z 46 and SDMA at m/z 172 respectively, followed by measuring the peak area/peak intensity ratios of the unique and common product ions to generate equi-molar concentration response curves for each individual isomer pair as a function of equimolar ratios;
c) subjecting a sample containing unknown concentrations of ADMA and SDMA isomers followed by measuring the unique to common product ion ratio(s), and determining the corresponding equimolar ratio(s) of the isomer pairs present based on the equimolar concentration response curve(s) generated in step (b).

Further, the equimolar reference mixture contains either a single pair of ADMA and SDMA isomers or multiple pairs of ADMA and SDMA isomers mixed together to make a single or several sets of reference equimolar mixture(s).

Accordingly, ADMA and SDMA gives rise to a single m/z peak at 203.1503, which is an $[M+H]^+$ adduct. The isomers cannot be discriminated based on their molecular ion or an adduct such as the $[M+H]^+$ alone. The exceptions are the unique product ion peaks at m/z 46 and 172 for ADMA and SDMA respectively.

The common ions were used instead of the internal standard. In the algorithm, product ions at m/z 46 and 172 were normalized with 116 (a common product ion). The algorithm then generated an equimolar calibration curve. A linear fit (y=0.0168x+0.0695, $R^2$=0.99) was obtained and this was further used for estimating the unknown values of samples.

The present invention provides a process for quantitatively determining isomers leucine and isoleucine comprising:
a) subjecting an equimolar mixture containing the reference isomers leucine and isoleucine to ionization and selecting precursor ions having a mass to charge ratio in an m/z range followed by fragmentation to generate product ions that are unique and common to leucine and isoleucine;
b) selecting a common ion at m/z 44 to normalize the ion unique to isoleucine at m/z 18 followed by measuring the peak area/peak intensity ratios of the unique and common product ions to generate concentration response curves for each individual isomer pair as a function of equimolar ratios; and
c) subjecting a sample containing unknown concentrations of leucine and isoleucine followed by measuring the unique to common product ion ratio(s), and determining the corresponding equimolar ratio(s) of the isomer pairs present based on the equimolar concentration response curve(s) generated in step (b).

Further, the equimolar reference mixture contains either a single pair of leucine and isoleucine isomers or multiple pairs of leucine and isoleucine mixed together to make a single or several sets of reference equimolar mixture(s).

Tandem MS/MS of isomer mixture precursor ion at m/z 132 yields a stable immonium ion at m/z 86 based on which the isomers cannot be distinguished. Further, MS/MS fragmentation of m/z 86 yields a common product ion pattern for Leu and Ile. Common product ions at m/z 30, 44, 57 and 69 are observed for Leu and Ile. m/z 30 is the most intense ion formed for Leu fragmentation whereas, m/z 69 is predominantly formed during Ile fragmentation, m/z 18 was only observed for Ile. m/z 18 was chosen as the diagnostic product ion and the common product ion at m/z 44 is used for normalization to generate the equimolar calibration curve. The invention provides a process for quantitatively determining isomers methylmalonic acid and succinic acid comprising:
a) subjecting an equimolar mixture containing the reference isomers methylmalonic acid and succinic acid to ionization and selecting precursor ions having a mass to charge ratio in an m/z range followed by fragmentation to generate product ions that are common and unique to methyl malonic acid and succinic acid;
b) selecting a common product ion at m/z 73 to normalize the product ions unique to succinic acid at m/z 98 followed by measuring the peak area/peak intensity ratios of the unique and common product ion to generate concentration response curves; and
c) subjecting a sample containing unknown concentrations of methylmalonic acid and succinic acid followed by measuring the unique to common product ion ratio(s), and determining the corresponding equimolar ratio(s) of the isomer pairs present based on the equimolar concentration response curve(s) generated in step (b).

Further, the equimolar reference mixture contains either a single pair of methylmalonic acid and succinic acid isomers or multiple pairs of methylmalonic acid and succinic acid mixed together to make a single or several sets of reference equimolar mixture(s).

The tandem mass spectrometry of the precursor ion at m/z 117 yields common product ions at m/z 26, 50, 73 and 88 Da. The only differentiating product ion for these molecules is m/z 98 arising from SA fragmentation.

In yet another preferred embodiment, the present invention provides that the analyte is a biological sample selected from urine, blood plasma or RBC from patient samples or any other such sources of the isomers.

The present invention provides an in-vitro process for diagnosing a disease caused by altered concentrations of structural isomers.

The present invention provides a method of diagnosing a disease caused by altered concentrations of ADMA and SDMA by measuring the ratio of the said isomers in a subject, the said process comprising:
a) isolating and providing a biological sample from a subject;
b) subjecting an equimolar mixture containing the reference isomers ADMA and SDMA to ionization and selecting precursor ions having a mass to charge ratio in an m/z range followed by fragmentation to generate product ions that are unique and common to ADMA and SDMA;
c) selecting a common product ion at m/z 116 to normalize the product ions unique to ADMA at m/z 46 and SDMA at m/z 172 followed by measuring the peak area/peak intensity ratios of the unique and common product ions to generate concentration response curves; and
d) subjecting a sample containing unknown concentrations of ADMA and SDMA isomers followed by measuring the unique to common product ion ratio(s), and determining the corresponding equimolar ratio(s) of the isomer pairs present based on the equimolar concentration response curve(s) generated step (b);
wherein altered ratio of ADMA:SDMA in the biological sample compared to the reference is indicative that the subject has, or is at a risk of developing a disease characterized by altered ratio of ADMA:SDMA.

Further, the disease characterized by altered ratio of ADMA:SDMA is a cardiovascular disease or a chronic kidney disease.

The present invention provides a method of diagnosing a disease caused by altered concentrations of leucine and isoleucine by measuring the ratio of the said isomers in a subject, the said process comprising:
a) isolating and providing a biological sample from a subject;
b) subjecting an mixture containing the reference isomers leucine and isoleucine selecting precursor ions having a mass to charge ratio in an m/z range followed by fragmentation to generate product ions that are unique and common to the leucine and isoleucine;
c) selecting a common product ion at m/z 44 to normalize the product ion unique to isoleucine at m/z 18 followed by measuring the peak area/peak intensity ratios of the unique and common product ions to generate concentration response curves; and
d) subjecting a sample containing unknown concentrations of leucine and isoleucine followed by measuring the unique to common product ion ratio(s), and determining the corresponding equimolar ratio(s) of the isomer pairs present based on the equimolar concentration response curve(s) generated step (b).
wherein altered ratio of leucine:isoleucine in the biological sample compared to the reference is indicative that the subject has, or is at a risk of developing a disease characterized by altered ratio of leucine:isoleucine.

The said disease characterized by altered ratio of leucine:isoleucine is a liver disorder, diabetes, maple syrup urine disease and obesity.

The present invention provides a method of diagnosing a disease caused by altered concentrations of methyl malonic acid and succinic acid by measuring the ratio of the said isomers in a subject, the said process comprising:
- a) isolating and providing a biological sample from a subject;
- b) subjecting an equimolar mixture containing the reference isomers methyl malonic acid and succinic acid to ionization and selecting precursor ions having a mass to charge ratio in an m/z range followed by fragmentation to generate product ions that are unique and common to methyl malonic acid and succinic acid;
- c) selecting a common product ion at m/z 73 to normalize the product ions unique to succinic acid at m/z 98 followed by measuring the peak area/peak intensity ratios of the unique and common product ion to generate concentration response curves; and
- d) subjecting a sample containing unknown concentrations of methyl malonic acid and succinic acid followed by measuring the unique to common product ion ratio(s), and determining the corresponding equimolar ratio(s) of the isomer pairs present based on the equimolar concentration response curve(s) generated step (b).

wherein altered ratio of methyl malonic acid and succinic acid in the biological sample compared to the reference is indicative that the subject has, or is at a risk of developing a disease characterized by altered ratio of methyl malonic acid and succinic acid.

The disease characterized by altered ratio of methyl malonic acid and succinic acid is selected from methyl malonic acidemia, vitamin B12 deficiency and pernicious anemia.

In another preferred embodiment the present invention provides a method of simultaneous MALDI MS/MS monitoring, for plasma, urine, saliva, tissue, cell and other biological samples.

The present invention provides a diagnostic kit for determination of structural isomers comprising:
- a) equimolar mixture of reference standards of isomer(s) pairs in vials and/or as dried precoated spots on a sample analysis plate,
- b) a CD with algorithm for determining the isomers quantitatively, and
- c) a detailed protocol to achieve this using the former together.

Present invention provides a kit comprising (Figure/Drawing 2):
- a. series containing mixture of isomers in varying ratios (labelled 1-8 in Figure/Drawing 2) (lyophilized, storage at −20° C. and shipping at −80° C.);
- b. three quality control samples in plasma or any such fluid from biological source or synthetically simulated, and standards (lyophilized, storage and shipping at −80° C. and labeled as U1-U3 and B1-B3 in Figure/Drawing 2);
- c. solutions/buffers (labeled as Buf1-Buf3); and/or
- d. a disposable MALDI target plate containing dried spots of equimolar quantities of clinical isomer pairs (CIP-ADMA/SDMA, Leu/Ile and MMA/SA) each along with space for samples to be analysed; and
- e. Software on a CD (labeled as 'Equi-MQ' in Figure/Drawing 2) and protocol to use as a Product Information Sheet is useful in a clinical laboratory.

In view of the above, the present invention provides a method for the determination of isomers ADMA and SDMA in a given sample. It is different from the other methods in the following aspects:
- (i) 'Equi-MQ' can determine ADMA catabolism index based on the varied ratios of ADMA and SDMA. Hence, it can be further used as a predictive tool in disease diagnosis.
- (ii) Quantitation using other tandem mass spectrometry based methods for these analytes relies on SRM and MRM where the calibration parameter (peak area/peak intensity) is normalized with a heavier isotope. The present method bypasses the use of an external labeled standard with a common product ion that arises from both ADMA and SDMA as in an equimolar mixture; considering the contribution of a common product ion would be same from both isomers.

High throughput analysis implies generation of large amount of experimental data and thus, software that can distinguish, quantify and estimate diagnostic values holding clinical significance.

EXAMPLES

Following examples are given by way of illustration therefore should not be construed to limit the scope of the invention.

Example 1

Quantification of Asymmetric Dimethyl Arginine (ADMA) and Symmetric Dimethyl Arginine (SDMA) Preparing Equimolar Mixtures of Synthetic Isomer Standards In this study, ADMA and SDMA were used as standards for providing the proof of concept. 100 μM stock solutions were prepared from the standards of ADMA and SDMA each. From 100 μM stock solutions, dilutions were prepared in a range of 0-10 μM and 10-0 μM for ADMA and SDMA respectively, and mixed together. The ratios in the mixtures were varied in the range of 0:10, 1:9, 2:8, 3:7, 4:6, 5:5, 6:4, 7:3, 8:2, 9:1 and 10:0 respectively. Calibration curves were prepared based on these mixtures.

Preparing Unknowns or Quality Control Standards

Quality control (QC) samples were prepared at three different ranges: low: 3.5:6.5, medium: 4.5:5.5 and high: 7.5:2.5 ratio of ADMA:SDMA. This was done to validate the calibration curve using these mixtures as unknown and demonstrating the method's utility.

Preparing Quality Control Samples in Plasma

The QC standards were spiked in plasma and proteins were precipitated using methanol. The supernatants were collected. This is also done to demonstrate the utility of method in biological fluids.

MALDI MS/MS of the Standards and Quality Control Samples

The calibrators, QC samples for standards and plasma were spotted on a 96 well MALDI target plate with 2,5-dihydrobenzoic acid (2,5-DHB) as matrix. The samples were left for drying and then, subjected to MALDI analysis. For MALDI MS analysis, MS/MS was performed in automated mode. For MS/MS, ion at m/z 203.1511 was selected to be fragmented with CID mode on. Analysis was performed on AB Sciex 5800 MALDI TOF/TOF system.

Data Processing and Quantitation

The instrumental files (.T2D files) were converted to ASCII files via an online module termed Proteomass. The ASCII files obtained were separated and clubbed according to the different concentration ranges in this case, isomer ratios. As shown in FIG. 1, m/z 203.1511 gives rise to different peaks in MS/MS mode. Out of these, m/z 46 is unique for ADMA and m/z 172 is unique for SDMA. Other product ions are common to both. These common product ions are used instead of the internal standard. In the algorithm, product ions at m/z 46 and 172 are normalized with 116 (a common product ion). The algorithm then generates a calibration curve. After generation of calibration curve, the QCs from standard and plasma are used as unknown files. The algorithm gives the values for the QC samples. Table 1 gives the estimation by software for the QC samples from standards and plasma samples. Lower RSD (relative standard deviation) means better reproducibility. A schematic in Figure/Drawing 3 illustrates the workflow used by the algorithm by determining (a) quantitative parameters such as peak area or intensity for the distinguishing as well as common product ions for the isomers, (b) building quantitative models for the isomers using common product ion as a normalizing factor and (c) quantitation of individual isomers from unknown or QC samples.

TABLE 1

Tabulated values obtained for an equimolar mixture of ADMA and SDMA

| Concentration of mixture (ADMA:SDMA) | Area under curve [ADMA]/[ADMA + SDMA] | % RSD | N |
|---|---|---|---|
| 0 | 0.0514 | 23.1 | 4 |
| 10 | 0.2841 | 14.6 | 6 |
| 20 | 0.4230 | 11.0 | 5 |
| 30 | 0.3855 | 12.2 | 5 |
| 40 | 0.5106 | 10.9 | 6 |
| 50 | 0.6323 | 9.5 | 5 |
| 60 | 0.5617 | 9.4 | 5 |
| 70 | 0.6796 | 15.7 | 6 |
| 80 | 0.6694 | 2.8 | 3 |
| 90 | 0.8484 | 14.2 | 5 |
| 100 | 1.1079 | 11.5 | 4 |

TABLE 2

Equimolar standard mixture of ADMA and SDMA analyzed in MALDI MS/M with recovery and % RSD

| Equimolar mixture (ADMA:SDMA) | ADMA recovery (% RSD) | | SDMA recovery (% RSD) | |
|---|---|---|---|---|
| | Standard | Plasma | Standard | Plasma |
| 35:65 | 117 (9.8) | 117 (13.0) | 102 (12.9) | 91 (9.1) |
| 55:45 | 87 (10.2) | 111 (17.2) | 115 (9.3) | 91 (17.3) |
| 75:25 | 99 (3.1) | 113 (5.6) | 102 (9.1) | 72 (11.3) |

Example 2

The developed method in the previous example was adapted to detect endogenous amounts of the analytes (ADMA and SDMA) from human subjects. The detectable ratios of the analytes are further compared with the absolute concentrations obtained earlier.

The mixtures for equimolar calibration curve were prepared in the same way as mentioned in example 1. Quality control (QC) samples were also prepared in a similar fashion at three different ranges: low: 3.5:6.5, medium: 5.5:4.5 and high: 7.5:2.5 ratio of ADMA:SDMA. This was done to validate the calibration curve using these mixtures as unknown and demonstrating the method's utility. Urine samples were collected with prior consent from eleven healthy volunteers following the Institutional Human Ethics Committee (IHEC) guidelines. 100 µL from each sample was collected in a tube and mixed well together to get a pooled sample and different aliquots were stored at −80° C. Cold methanol was added for precipitation of proteins followed by vortexing and centrifugation at 13,200 rpm for 15 minutes at 4° C. The supernatant is collected. The sample was further diluted 10 times with cold methanol before subjecting to MALDI MS analysis and determining the isomer mass spectral peak ratios. The lowest and highest QC samples were also spiked (standard addition method) in the pooled urine sample to validate the method for its accuracy and precision.

The calibrators, QC samples for standards and urine samples were spotted on a 96 well MALDI target plate with 2,5-dihydrobenzoic acid (2,5-DHB) as matrix. The samples were left for drying and then, subjected to MALDI analysis. For MALDI MS analysis, MS/MS was performed in automated mode. For MS/MS, ion at m/z 203.1511 was selected to be fragmented with CID mode on. Analysis was performed on AB Sciex 5800 MALDI TOF/TOF system. The instrumental files (.T2D files) were converted to ASCII files. The ASCII files obtained were separated and clubbed according to the different concentration ranges in this case, isomer ratios. As shown in the earlier example, m/z 203.1511 gives rise to different peaks in MS/MS mode. Out of these, m/z 46 is unique for ADMA and m/z 172 is unique for SDMA. Other product ions are common to both. These common product ions are used instead of internal standard. In the algorithm, product ions at m/z 46 and 172 are normalized with 116 (a common product ion). The algorithm then generates a equimolar calibration curve. A linear fit (y=0.0168x+0.0695, $R^2$=0.99) was obtained and this was further used for estimating the unknown values of QC samples. Table 3 summarizes the estimation by software for the QC samples from standards and urine samples. Lower RSD (relative standard deviation) indicates better reproducibility of the method. The recoveries for the standard QC samples and of those spiked in pooled urine (standard addition method) were within 91-117% with excellent % RSD (within 15% as per FDA guidelines) for n=4 replicates. The ratio of ADMA/SDMA observed from pooled urine was 0.54 (% RSD—14.0) that correlates well with the ratio observed earlier with absolute concentration (Table 3). These results and comparison unambiguously demonstrate that the method developed with the equimolar mixture can indeed be used for detecting the isomer ratios from clinically relevant samples without using an internal standard. Biological samples are often prone to degradation, instability and reactivity. Monitoring the ratio of isomers would also help in establishing stability studies. This method can also be used for routine screening of clinical samples and monitor the ratios of isomers from a clinically relevant context.

TABLE 3

Validation of the ADMA:SDMA isomer analysis method using standard quality control (QC) samples and isomer ratios from pooled urine samples of 11 healthy individuals following MALDI MS/MS analysis:

| Molar ratio of QC samples | ADMA recovery (% RSD) | | SDMA recovery (% RSD) | | Estimation of ADMA:SDMA from urine samples (n = 11) | |
|---|---|---|---|---|---|---|
| | | | | | Ratio obtained using internal standard method[#] | Ratio obtained using equimolar method (no internal standard) |
| (ADMA:SDMA) | Standard | Urine* | Standard | Urine* | | |
| 35:65 | 117 (8.5) | 96 (6.7) | 91 (5.8) | 104 (6.5) | 0.41 | 0.54 |
| 75:25 | 98 (2.1) | 99 (3.9) | 107 (5.8) | 101 (2.8) | | |

*QC samples added to urine (standard addition method) for estimation of method accuracy. Values indicate only for the added amount recovery;
[#]The observed concentrations with absolute quantitation for ADMA and SDMA in urine were 5.8 and 14.1 µM respectively Example 3

Quantification of Leucine (Leu) and Isoleucine (Ile)

Figure 4:
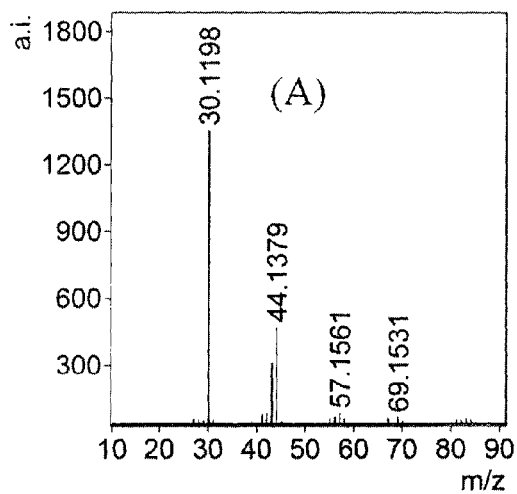
FIG. 4 depicts Immonium ion (m/z 86), a common product ion to both isomers leucine and isoleucine in the MALDI MS mode itself. Different MS/MS fragmentation patterns were observed for the immonium ion for (A) Leu and (B) Ile showed. Product ion at m/z 18 is unique to only Ile while m/z 30, 44, 57 and 69 are common to both the isomers. Product ions at m/z 30 and 69 are present in different ratios for Leu and Ile, respectively.
Figure 4:
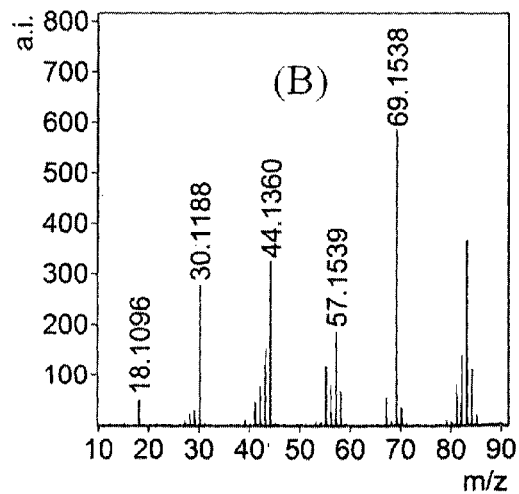

The equimolar mixture analysis was demonstrated with another set of structural isomers Leu and Ile. Equimolar mixtures as mentioned in earlier examples were also used in this example. Leu and Ile in the ratio of 1:9, 2:8, 4:6, 6:4, 7:3 and 9:1 were used as calibrators. Mixtures in the ratio of 3:7, 5:5 and 8:2 were used as QC/unknown samples. α-Cyano-4-hydroxycinnamic acid (CHCA) was used as matrix for this analysis. Analysis was performed on AB Sciex 5800 MALDI-TOF/TOF instrument. Tandem MS/MS of their precursor ion at m/z 132 yielded a stable immonium product ion at m/z 86 based on which the isomers cannot be distinguished. This product ion (m/z 86) was observed in single stage MS mode. FIGS. 4(A & B) shows further MS/MS fragmentation (pseudo MS$^3$) pattern of m/z 86 for Leu and Ile. Common product ions at m/z 30, 44, 57 and 69 were observed for Leu (FIG. 4A) and Ile (FIG. 4B). The common product ions at m/z 30 and 69 were observed with both the isomers but vary in intensity. m/z 30 was the most intense product ion formed for Leu fragmentation whereas, m/z 69 was predominantly formed during Ile fragmentation. Interestingly, m/z 18 was only observed for Ile (FIG. 4B).

m/z 18 was chosen as the diagnostic product ion and the common product ion at m/z 44 was used for normalisation to generate the equimolar calibration curve. The recoveries along with % RSD for QC samples are provided in Table 4. The QC samples showed recoveries within 88-120% along with good % RSD (within 20%). This example shows the applicability of the method in estimating the isomers even when only one distinguishing fragment for the isomers is present.

TABLE 4

Validation of the L-Leucine and L-Isoleucine isomer analysis method using standard quality control (QC) samples of equimolar synthetic mixture following MALDI MS/MS

| Equimolar mixture (Leu:Ile) | Leu recovery (% RSD) | Ile recovery (% RSD) |
|---|---|---|
| 30:70 | 120 (4.5) | 91 (2.5) |
| 50:50 | 88 (16.3) | 112 (12.8) |
| 80:20 | 100 (3.5) | 100 (14.1) |

Example 4

Quantification of Methylmalonic Acid (Mma) and Succinic Acid (Sa)

Figure 5:
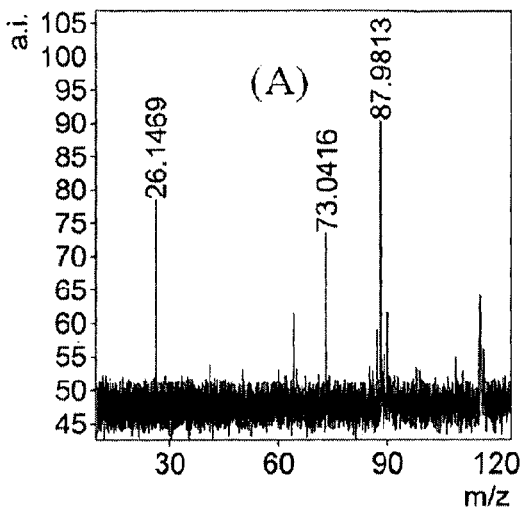
FIG. 5 depicts MS/MS of (A) MMA and (B) SA product ions at m/z 26, 73 and 87 common to methylmalonic acid (MMA) and succinic acid (SA) and m/z 98 that is unique for SA.
Figure 5:
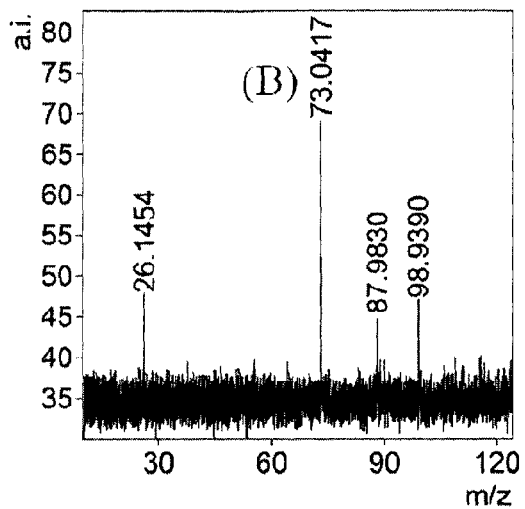
Figure 6:
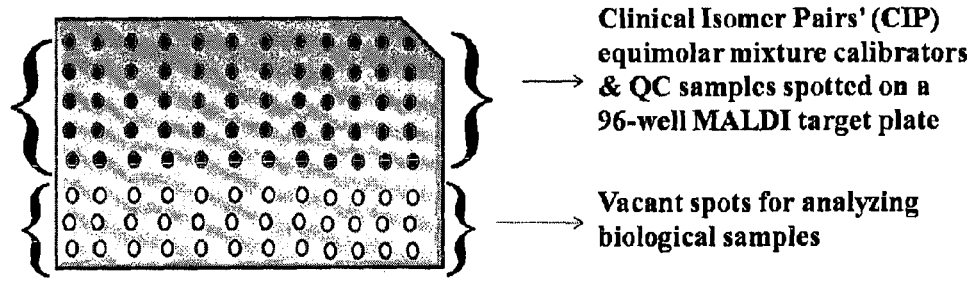
FIG. 6 depicts a kit comprising of a 96 well MALDI target plate containing dried spots of a series of calibrators and QC samples for clinical isomer pairs' (CIP-ADMA/SDMA, Leu/Ile and MMA/SA) mixture. There are vacant spots for analyzing biological samples. Similar example can be highlighted with a 384 well MALDI target plate.

Analysis of another class of isomers MMA and SA is demonstrated in this example. These are dicarboxylic acids implicated in different diseases and are detectable in negative ion mode. 9-aminoacridine was used as a matrix for analysis. MALDI analysis was done on AB Sciex 5800 MALDI-TOF/TOF instrument. The tandem mass spectrometry of the precursor ion at m/z 117 yields common product ions at m/z 26, 50, 73 and 88 Da. The only differentiating product ion for these molecules is m/z 98 arising from SA fragmentation as shown in FIG. 5. m/z 73 was chosen as the common product ion and m/z 98 was chosen as the unique product ion during analysis.

MMA and SA in the ratio of 1:9, 3:7, 4:6, 5:5, 6:4, 7:3, 8:2 and 9:1 were used as calibrators. Mixtures in the ratio of 2:8, 3.5:6.5 and 7.5:2.5 were used as QC samples. Table 5 shows the recoveries along with % RSD for the QC samples. The samples showed recoveries within the range of 66-111%. The % RSD for two samples was higher than 20%. The remaining samples showed excellent % RSD within 15%. This example proves the applicability of the method irrespective of the ionization mode.

TABLE 5

Validation of the methylmalonic acid (MMA) and succinic acid (SA) isomer analysis method using standard quality control (QC) samples of equimolar synthetic mixture following MALDI, MS/MS

| Equimolar mixture (MMA:SA) | MMA recovery (% RSD) | SA recovery (% RSD) |
|---|---|---|
| 20:80 | 98 (22.5) | 101 (5.5) |
| 35:65 | 98 (3.8) | 101 (1.7) |
| 75:25 | 111 (5.1) | 66 (25.8) |

ADVANTAGES OF THE INVENTION

Chromatography free
Internal standard (labelled or otherwise) free
Analyte concentration independent
Can be used even if one diagnostic product ion of an isomer is present for the samples
High-throughput method applicable in all MS/MS modes
No need of complex sample preparation steps
Algorithm is user-friendly, and
The present invention does not use any single or multiple reaction monitoring schemes (MRM or SRM). Any ion reaction monitoring scheme employs ion selection filter that causes possible ion losses thereby, reducing sensitivity, they also suffer from unit resolution and hence, poor mass accuracies.

We claim:

1. A method for quantitatively determining structural isomers comprising:
   a) subjecting an equimolar mixture containing the reference isomers to ionization and selecting precursor ions having a mass to charge ratio in an m/z range between 1 to 40000 (z=1) followed by fragmentation to generate product ions that are both common and unique in nature to the reference isomers;
   b) selecting product ions that are common to the isomer pairs to normalize the unique product ions followed by measuring the peak area/peak intensity ratios of the unique and common product ions to generate equimolar concentration response curves for each individual isomer pair as a function of equimolar ratios; and
   c) subjecting a sample containing unknown quantities of the isomers/isomer pairs in context to ionization and selecting precursor ions having a mass to charge ratio in an m/z range between 1 to 40000 (z=1) followed by fragmentation to generate product ions that are both common and unique in nature as in step (a); measuring the unique to common product ion ratio(s), and determining the corresponding equimolar ratio(s) of the isomer pairs present based on the equimolar concentration response curve(s) generated in step (b).

2. The method according to claim 1, wherein the common product ion production is achieved in the ionization step of (c) of claim 1 where needed by adding a known predetermined quantity of a common product ion producing non endogenous synthetic isomer(s) to a sample containing unknown quantities of one or more of the isomers/isomer pairs in context followed by ionization and selecting precursor ions having a mass to charge ratio in an m/z range between 1 to 40000 (z=1) followed by fragmentation to generate product ions that are both common and unique in nature as in step (a); measuring the unique to common product ion ratio(s), and determining the corresponding equimolar ratio(s) of the isomer pairs present based on the equimolar concentration response curve(s) generated in step (b).

3. The method according to claim 1, wherein the equimolar reference mixture is selected from a single pair of isomers and/or multiple pairs of different isomers mixed together to make a single or several sets of reference equimolar mixture(s).

4. The method according to claim 1, wherein the analyte is subjected to MALDI MS/MS or LDI MS/MS analysis.

5. The method according to claim 1, wherein the common product ions are from the analyte or a different analyte fragmenting together with analyte.

6. The method according to claim 1, wherein the peak area/peak intensity ratios of unique and common product ions to generate concentration response curves are based on the ASCII files.

7. The method according to claim 1, wherein the isomers are selected from the group consisting of asymmetric dimethyl arginine (ADMA) and symmetric dimethyl arginine (SDMA); leucine and isoleucine; methyl malonic acid (MMA) and succinic acid (SA); bilirubin and lumirubin and the like.

8. The method according to claim 1, wherein the sample is a biological sample selected from urine, blood sample, blood plasma and RBC from patient samples or any other such sources of the isomers.

9. The method for quantitatively determining structural isomers as claimed in claim 1, for use in diagnostic kit for determination of structural isomers comprising:
   a) equimolar mixture of reference standards of isomer(s) pairs in vials and/or as dried precoated spots on a sample analysis plate,
   b) a common product ion producing non endogeneous synthetic isomer (s)
   c) a CD with algorithm for determining the isomers quantitatively, and
   d) a detailed protocol to achieve this using the former together.

10. The method for quantitatively determining structural isomers as claimed in claim 9, the diagnostic kit comprising:
    a) a series of mixture of isomers in varying ratios;
    b) three quality control samples in plasma or any such fluid from biological source or synthetically simulated and standards;
    c) solutions/buffers (labeled as Buf1-Buf3); and/or
    d) common product ion producing non endogeneous synthetic isomer(s)
    e) a disposable MALDI target plate containing dried spots of Clinical Isomer Pairs (CIP-ADMA/SDMA, Leu/Ile and MMA/SA) mixture along with space for samples to be analyzed; and
    f) software on a CD and instructions to use the kit contained in a Product Information Sheet.

11. A method of diagnosing a disease caused by altered concentrations of isomer ratio by measuring the ratio of the isomers in a biological sample, which process comprises:
    a) isolating and providing a biological sample from a subject;
    b) subjecting an equimolar mixture containing the reference isomers to ionization and selecting precursor ions having a mass to charge ratio in an m/z range between 1 to 400000 (z=1) followed by fragmentation to generate product ions that are both common and unique in nature to the reference isomers;
    c) selecting product ions that are common to the isomer pairs to normalize the unique product ions followed by measuring the peak area/peak intensity ratios of the unique and common product ions to generate equimolar concentration response curves for each individual isomer pair as a function of equimolar ratios; and d) subjecting a sample containing unknown quantities of the isomers/isomer pairs in context to ionization and selecting precursor ions having a mass to charge ratio in an m/z range between 1 to 40000 (z=1) followed by fragmentation to generate product ions that are both common and unique in nature as in step (a); measuring the unique to common product ion ratio(s), and determining the corresponding equimolar ratio(s) of the isomer pairs present based on the equimolar concentration response curve(s) generated in step (b)

wherein altered ratio of isomers in the biological sample compared to the reference is indicative that the subject has, or is at a risk of developing a disease characterized by altered ratio of the isomer.

12. The method according to claim 11, wherein the common product ion production is achieved in the ionization step of (c) of claim 11 where needed by adding a known predetermined quantity of a common product ion producing non endogeneous synthetic isomer(s) to a biological sample isolated from a human subject or other non human biological specimen containing unknown quantities of one or more of the isomers/isomer pairs in context followed by ionization and selecting precursor ions having a mass to charge ratio in an m/z range between 1 to 40000 (z=1) followed by fragmentation to generate product ions that are both common and unique in nature as in step (a); measuring the unique to common product ion ratio(s), and determining the corresponding equimolar ratio(s) of the isomer pairs present based on the equimolar concentration response curve(s) generated in step (b).

13. The method of diagnosing a disease according to claim 11, wherein the disease is a cardiovascular disease or a chronic kidney disease, liver disorders, maple syrup urine disease, diabetes, obesity, methylmalonic acidemia, vitamin B12 deficiency and pernicious anemia.

* * * * *